(12) United States Patent
Nishimura (10) Patent No.: US 9,649,360 B2
(45) Date of Patent: May 16, 2017

(54) PHARMACEUTICAL COMPOSITION FOR THE TREATMENT AND/OR PREVENTION OF DISEASE INVOLVING ABNORMAL ACCUMULATION OF AMYLOID β PROTEIN

(71) Applicant: SHIGA UNIVERSITY OF MEDICAL SCIENCE, Shiga (JP)

(72) Inventor: Masaki Nishimura, Shiga (JP)

(73) Assignee: Shiga University of Medical Science, Shiga (JP)

( * ) Notice: Subject to any disclaimer, the term of this patent is extended or adjusted under 35 U.S.C. 154(b) by 0 days.

(21) Appl. No.: 14/653,442

(22) PCT Filed: Dec. 13, 2013

(86) PCT No.: PCT/JP2013/083435
§ 371 (c)(1),
(2) Date: Jun. 18, 2015

(87) PCT Pub. No.: WO2014/097978
PCT Pub. Date: Jun. 26, 2014

(65) Prior Publication Data
US 2016/0184397 A1    Jun. 30, 2016

(30) Foreign Application Priority Data
Dec. 19, 2012    (JP) ................. 2012-277068

(51) Int. Cl.
*A61K 38/17* (2006.01)
*A61K 38/19* (2006.01)
*G01N 33/50* (2006.01)
*G01N 33/68* (2006.01)
*A61K 48/00* (2006.01)

(52) U.S. Cl.
CPC ......... *A61K 38/19* (2013.01); *G01N 33/5008* (2013.01); *G01N 33/5023* (2013.01); *G01N 33/5041* (2013.01); *G01N 33/6896* (2013.01); *A61K 48/00* (2013.01); *G01N 2333/4709* (2013.01); *G01N 2333/54* (2013.01); *G01N 2800/2821* (2013.01)

(58) Field of Classification Search
CPC ........ A61K 38/19; A61K 48/00; A61K 38/55; A61K 38/57
See application file for complete search history.

(56) References Cited

U.S. PATENT DOCUMENTS 7,312,079 B1 * 12/2007 Hu ................. C12N 9/1048
                                                          435/252.3
7,993,868 B2 * 8/2011 Davies ............... G01N 33/6896
                                                          435/7.1
8,609,612 B2 * 12/2013 Cao ..................... A61K 38/17
                                                          514/6.7

FOREIGN PATENT DOCUMENTS

| JP | 2008-537143 A | 9/2008 |
| WO | 02/063009 A2 | 8/2002 |
| WO | 2006/113289 A2 | 10/2006 |
| WO | 2011/100197 A1 | 8/2011 |

OTHER PUBLICATIONS

Hampel H et al. The future of Alzheimer's disease: the next 10 years. Progress Neurobiol. 2011, 95:718-728.*
Hasegawa H et al. The FAM3 superfamily member ILEI ameliorates Alzheimer's disease-like pathology by destabilizing the penultimate amyloid-beta precursor. Nat. Comm. 2014, 5:3917 (pp. 1-13).*
Juengst ET. What next for human gene therapy? BMJ, 2003, 326: 1410-1411.*
Kay Ma et al. Viral vectors for gene therapy: the art of turning infectious agents into vehicles of therapeutics. Nature Med. 2001, 7(1): 33-40.*
Lemere CA et al. Amyloid-beta immunotherapy for the prevention and treatment of Alzheimer disease: lessons from mice, monkeys and humans. Rejuvenation Res. 2006; 9(1):77-84.*
Liu Y et al. Amyloid beta peptide alters intracellular vesicle trafficking and cholesterol homeostasis. Proc Natl Acad Sci USA, 1998; 95:13266-13271.*
Masliah E et al. Amyloid protein precursor stimulates excitatory amino acid transport. J. Biol. Chem. 1998; 273(20):12548-12554.*
Pardridge WM. The blood-brain barrier: Bottleneck in brain drug development. NeuroRx, 2005, 2(1):3-14.*
Patil SD et al. DNA-based therapeutics and DNA delivery systems: a comprehensive reivew. The AAPS Journal, 2005, 7(1): Article 9, E61-E77.*
Perez RG et al. The beta-amyloid precursor protein of Alzheimer's disease enhances neuron viability and modulates neuronal polarity. J. Neurosci. 1997; 17:9407-9414.*
Plant Le et al. The production of amyloid beta peptide is a critical requirement for the viability of central neurons. J. Neurosci. 2003; 23:5531-5535.*
Small DH. The role of the amyloid precursor protein (APP) in Alzheimer's disease: does the normal function of APP explain the topgraphy of neurodegeneration? Neurochem. Res. 1998; 23(5):795-806.*
Trent et al. Chapter 6, Genetics and Cellular Therapies from Molecular Med: An Introductory Text, 2005, pp. 143-173.*
Vickers JC. A vaccine against Alzheimer's disease: developments to date. Drugs Aging. 2002; 19(7):487-494.*
Waerner T et al. ILEI: a cytokine essential for EMT, tumor formation, and late events in metastasis in epithelial cells. Cancer Cell, 2006, 10:227-239.*

* cited by examiner

*Primary Examiner* — Kimberly A. Ballard
(74) *Attorney, Agent, or Firm* — Morgan, Lewis & Bockius LLP (57) ABSTRACT

Disclosed is a pharmaceutical composition for the treatment and/or prevention of a disease involving abnormal accumulation of amyloid β protein comprising ILEI, or a vector into which a polynucleotide encoding ILEI is inserted; a method for screening a compound for the treatment and/or prevention of a disease involving abnormal accumulation of amyloid β protein; and a method for treating and/or preventing a disease involving abnormal accumulation of amyloid β protein.

6 Claims, 2 Drawing Sheets

PHARMACEUTICAL COMPOSITION FOR THE TREATMENT AND/OR PREVENTION OF DISEASE INVOLVING ABNORMAL ACCUMULATION OF AMYLOID β PROTEIN

SEQUENCE LISTING SUBMISSION VIA EFS WEB

A computer readable text file, entitled "020463-5006_SequenceListing.txt," created on or about Jun. 16, 2015 with a file size of about 6 KB contains the sequence listing for this application and is hereby incorporated by reference in its entirety.

TECHNICAL FIELD

The present invention relates to a pharmaceutical composition for the treatment and/or prevention of a disease involving abnormal accumulation of amyloid β protein. Further, the present invention relates to a method for screening a compound for the treatment and/or prevention of a disease involving accumulation of amyloid β protein.

BACKGROUND ART

Abnormal accumulation of amyloid β protein (Aβ) in brain is implicated in the molecular pathogenesis of Alzheimer's disease (AD). Therefore, decreasing Aβ is expected to serve as a treatment of Alzheimer's disease based on the pathological condition.

Figure 4:
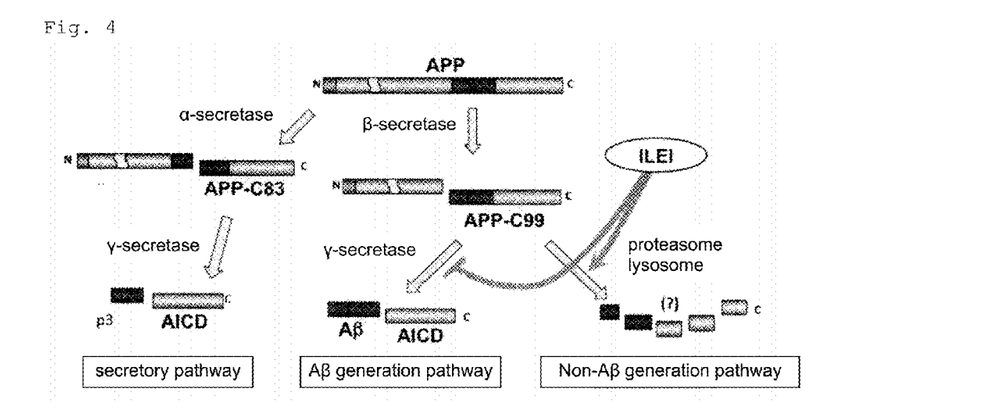
FIG. 4 shows Aβ generation pathways from APP.

Aβ is produced in neuron cells by a two-step proteolytic processing of the amyloid-β precursor protein (APP). The initial cleavage at the extracellular juxtamembrane site is mediated by the β-secretase, and yields the secretory N-terminal ectodomain (sAPPβ) and the membrane-spanning C-terminal fragment (APP-CTFβ or APP-C99). Then, the intramembranous aspartyl protease γ-secretase (a macromolecular complex comprised of four core components: presenilin, nicastrin, anterior pharynx defective-1 (APH-1) and presenilin enhancer-2 (PEN-2)) further proteolyzes APP-C99 to Aβ and the APP intracellular domain (AICD) (see FIG. 4). For APP-C99 proteolysis, a pathway that does not involve Aβ generation is also known.

In the development of the therapeutic strategy for Alzheimer's disease, γ-secretase activity inhibitors have been mainly used as a method for reducing Aβ generation from APP. Although many inhibitors have been developed, the clinical trials revealed that administration of γ-secretase inhibitors caused side effects such as worsening of dementia or increase in frequency of occurrence of skin cancer, presumably due to intracellular accumulation of APP-C99 and failure of cleavage of Notch protein that serves as a substrate as with APP.

Patent Document 1 discloses a biomarker for Alzheimer's disease. More specifically, Patent Document 1 is an invention that relates to a method for qualifying a state of Alzheimer's disease in a test subject; the method comprising (a) a step of measuring at least one biomarker in a biological material obtained from the test subject, wherein the at least one biomarker is selected from saposin D(I), saposin D(II), saposin D(III) and FAM3C(I); and a step (b) of relating the measurement result with a state of Alzheimer's disease.

However, Patent Document 1 merely discloses using the four kinds of protein as biomarkers for Alzheimer's disease, and nowhere discloses other uses thereof.

CITATION LIST

Patent Documents

Patent Document 1: JP2008-537143A

SUMMARY OF INVENTION

Technical Problem

An object of the present invention is to provide a pharmaceutical composition for the treatment and/or prevention of a disease involving abnormal accumulation of amyloid β protein comprising a protein that reduces Aβ generation without inhibiting Notch cleavage, or a vector into which a polynucleotide encoding the protein is inserted.

Another object of the present invention is to provide a method for screening a compound that increases the expression level of the protein that reduces Aβ generation without inhibiting Notch cleavage.

Still another object of the present invention is to provide a method for screening a compound having activity similar to that of the protein that reduces Aβ generation without inhibiting Notch cleavage.

Solution to Problem

The inventors of the present invention conducted extensive research to solve the above problems, and identified ILEI (interleukin-like epithelial-mesenchymal transition inducer; also referred to as family with sequence similarity 3, member C (FAM3C)) as a protein having Aβ generation-decreasing activity by promoting APP-C99 degradation in a non-Aβ generation pathway. The inventors also found that in addition to such characteristic activity, the ILEI is a secretory protein, and that, when a recombinant ILEI protein, which is produced using a cultured animal cell, acts from the outside of the cells, Aβ generation in the cultured cells can be decreased in a dose-dependent manner by similar activity. With this finding, the inventors completed the present invention.

The present invention was made by conducting further research based on these findings, and provides the following pharmaceutical compositions, screening methods, and treatment and/or prevention methods.

(I) Pharmaceutical Composition (I-1) A pharmaceutical composition for the treatment and/or prevention of a disease involving abnormal accumulation of amyloid β protein, the pharmaceutical composition comprising ILEI, or a vector into which a polynucleotide encoding ILEI is inserted.

(I-2) The pharmaceutical composition according to (I-1), wherein the disease involving abnormal accumulation of amyloid β protein is Alzheimer's disease.

(I-3) Use of ILEI, or a vector into which a polynucleotide encoding ILEI is inserted for the manufacture of a pharmaceutical composition for the treatment and/or prevention of disease involving abnormal accumulation of amyloid β protein.

(II) Screening Method 1

(II-1) A method for screening a compound for the treatment and/or prevention of a disease involving abnormal accumulation of amyloid β protein, comprising:

(1) contacting a candidate compound with a cell that expresses ILEI; and (2) selecting a compound that increases ILEI expression level, compared with the case where the candidate compound is not present.

(II-2) The method according to (II-1), wherein the disease involving abnormal accumulation of amyloid β protein is Alzheimer's disease.

(III) Screening Method 2

(III-1) A method for screening a compound that is used for the treatment and/or prevention of a disease involving abnormal accumulation of amyloid β protein and that has activity similar to that of ILEI, comprising:

(1) contacting a candidate compound with a cell that produces amyloid β protein; and (2) selecting a compound that reduces generation of amyloid β protein and also reduces APP-CTF (amyloid-β precursor protein C-terminal fragment) without inhibiting Notch cleavage, compared with the case where the candidate compound is not present.

(III-2) The method according to (III-1), wherein the disease involving abnormal accumulation of amyloid β protein is Alzheimer's disease.

(IV) Treatment and/or Prevention Method (IV-1) A method for treating and/or preventing a disease involving abnormal accumulation of amyloid β protein, comprising administering ILEI, or a vector into which a polynucleotide encoding ILEI is inserted.

(IV-2) The method according to (IV-1), wherein the disease involving abnormal accumulation of amyloid β protein is Alzheimer's disease.

Advantageous Effects of Invention

The pharmaceutical composition of the present invention has an excellent effect that it acts from the outside of the cell and reduces Aβ generation of the cell by selectively decreasing APP-C99 without inhibiting Notch cleavage. Therefore, the composition is capable of preventing progression of a disease involving abnormal accumulation of amyloid β protein (in particular Alzheimer's disease) and treating the disease, and is also capable of avoiding side effects confirmed in the administration of γ-secretase inhibitors.

Further, by using ILEI, it becomes also possible to screen a compound for preventing progression of a disease involving abnormal accumulation of amyloid β protein (in particular Alzheimer's disease), and for treating the disease.

DESCRIPTION OF EMBODIMENTS

The present invention is explained below in detail.

In the present invention, examples of the diseases involving abnormal accumulation of amyloid β protein includes Alzheimer's disease and Down's syndrome.

ILEI

The present inventors screened proteins that bind to a γ-secretase complex, and identified ILEI as one of such proteins. The present inventors further analyzed ILEI in a cultured cell, and found that (i) ILEI reduces Aβ generation, that (ii) although ILEI binds to a γ-secretase complex, it has no influence on its activity, that (iii) ILEI reduces the level of APP-C99, which is an intermediate produced during the generation of Aβ, that (iv) ILEI does not inhibit Notch cleavage, that (v) ILEI reduces brain Aβ when it is forcibly expressed in a mouse using a transgenic technology, etc.

ILEI is a secretory protein that was originally identified by a database search for a cytokine-like structure having a four-helix-bundle structure, and is evolutionally well-conserved. The signal sequence of the full-length precursor protein is cleaved off after ILEI is translated, and ILEI is liberated from the membrane in secretory vesicles.

In the specification, "ILEI" means a protein unless otherwise specified.

The amino acid sequence of ILEI is represented by, for example, SEQ ID NO: 1 (GenBank Accession No. NP_055703). The positions 1 to 24 in SEQ ID NO: 1 represent a signal peptide. The mature protein is a protein having an amino acid sequence (SEQ ID NO: 2) represented by positions 25 to 227 of SEQ ID NO: 1.

The ILEI in the present invention encompasses both a full-length protein and a mature protein.

In the present invention, ILEI may be a mutant of a protein having the amino acid sequence represented by SEQ ID NO: 1 or 2, insofar as the mutant has biological activity equivalent to that of the protein having the amino acid sequence represented by SEQ ID NO: 1 or 2.

Examples of the mutant include a protein having an amino acid sequence in which 1, or 2 or more, for example, 1 to 50, 1 to 25, 1 to 12, 1 to 9, or 1 to 5 amino acids in the amino acid sequence represented by SEQ ID NO: 1 or 2 are substituted, deleted, or added.

ILEI has significantly distinctive bioactivity such that it reduces Aβ generation by selectively reducing APP-C99, without inhibiting Notch cleavage. Such a characteristic has not been reported in the past. Further, ILEI is capable of acting from the outside of the cell.

Pharmaceutical Composition

The present invention is a pharmaceutical composition for the treatment and/or prevention of a disease involving abnormal accumulation of amyloid β protein. The composition of the present invention is characterized by comprising ILEI, or a vector into which a polynucleotide encoding ILEI is inserted.

A mature protein that does not have a signal sequence is preferably used as ILEI.

ILEI may be produced according to a known protein production process, for example, by obtaining the gene according to known gene sequence information and producing a transformant. The purification of the produced ILEI may be performed by affinity chromatography, ion-exchange chromatography, hydroxyapatite column chromatography, ammonium sulfate salting-out, or the like.

When a vector is used, it is preferable to use a polynucleotide encoding secretory ILEI having a signal sequence. The secreted ILEI can suppress the Aβ generation by acting from the outside of the cell. The polynucleotide encoding ILEI may be produced by a known polynucleotide production process. For example, the polynucleotide encoding ILEI may be produced by chemical synthesis of polynucleotide based on the ILEI gene sequence information, or by PCR using a primer capable of amplifying ILEI gene and complementary DNA (cDNA) as a template. Examples of the vector include adenovirus vector, retrovirus vector, lentivirus vector, adeno-associated viral vector, and the like. The vector may be administered in vivo or ex vivo.

The pharmaceutical composition of the present invention is administered to mammalians including humans. The pharmaceutical composition of the present invention may be administered systemically or locally. The administration method is not particularly limited; the composition is administered orally or parenterally. Examples of the route of parenteral administration include subcutaneous, intraperitoneal, intravenous, and intra-arterial injection or intravenous drip, injection or intravenous drip into cerebrospinal fluid or cerebral ventricles, and transdermal administration.

The pharmaceutical composition of the present invention has a pharmaceutically acceptable form suitable for administration to humans, and contains physiologically acceptable additives. As necessary, it is possible to add a pharmaceutically acceptable diluent, buffer, solubilizer (e.g., cyclodextrin, polyethylene glycol, or surfactant such as Tween, Pluronic, Cremophor, phospholipid, or the like), soothing agent, and the like, to the pharmaceutical composition. Further, as necessary, the composition may contain a pharmaceutically acceptable solvent, stabilizer, antioxidant (e.g., ascorbic acid), and the like. The administration method, the dosage form, etc., of the pharmaceutical composition of the present invention are suitably selected to ensure a concentration in which ILEI effectively suppresses the Aβ generation at or near the target cell. The dosage of the pharmaceutical composition of the present invention is suitably selected according to the usage, the age, sex, and other conditions of the patient, and the severity of the disease.

The ILEI content in the pharmaceutical composition of the present invention may be suitably selected from the range of 0.01 to 100 wt %, preferably from the range of 0.1 to 100 wt %.

The pharmaceutical composition of the present invention is capable of preventing the progress of disease involving abnormal accumulation of amyloid β protein (in particular Alzheimer's disease), and is also capable of treating the disease. Further, because ILEI does not inhibit the Notch cleavage, it is possible to avoid the side effects caused by the administration of γ-secretase inhibitor.

Screening Method 1

The method for screening the compound of the present invention for the treatment and/or prevention of a disease involving abnormal accumulation of amyloid β protein comprises:
(1) contacting a candidate compound with a cell that expresses ILEI; and
(2) selecting a compound that increases ILEI expression level, compared with the case where the candidate compound is not present.

The cell is not particularly limited insofar as it expresses ILEI; examples thereof include a cell in which ILEI gene is introduced.

The candidate compound is not particularly limited; examples thereof include low-molecular-weight compounds, high-molecular-weight compounds, biopolymers (protein, nucleic acid, polysaccharide, etc.), and the like. Various compound libraries having these compounds may be used.

The ILEI expression level when a candidate compound is brought into contact with a cell is compared with the case where the candidate compound is not present, and if the ILEI expression level is increased by 10% or more, preferably 25% or more, more preferably 50% or more, further preferably 75% or more, the compound may be selected as a compound effective for the treatment and prevention of a disease involving abnormal accumulation of amyloid β protein.

Detection of the ILEI expression level is performed by a method of detecting mRNA encoding ILEI or detecting ILEI itself. The extraction of mRNA or protein from a biological sample can be performed according to the standard method.

The method for detecting mRNA is not particularly limited insofar as it is capable of quantitative determination of mRNA; examples of the method include DNA Chip method, real-time PCR, and northern blotting. The mRNA detection method also includes detection of cDNA corresponding to the mRNA.

The method for detecting protein is not particularly limited insofar as it is capable of quantitative determination of protein; examples include analysis methods using ELISA, protein chip, western blotting, and the like.

The compound that can increase ILEI expression selected from the above method may be effective for the treatment and prevention of a disease involving abnormal accumulation of amyloid β protein (in particular, Alzheimer's disease).

Screening Method 2

The method for screening a compound that is used for the treatment and/or prevention of a disease involving abnormal accumulation of amyloid β protein and that has activity similar to that of ILEI of the present invention comprises:
(1) contacting a candidate compound with a cell that produces amyloid β protein; and
(2) selecting a compound that reduces generation of amyloid β protein and also reduces APP-CTF without inhibiting Notch cleavage, compared with the case where the candidate compound is not present.

These cell and candidate compounds are the same as those used above.

A compound satisfying all of the following conditions (a) to (b) can be selected as a compound that is effective for the treatment and prevention a disease involving abnormal accumulation of amyloid β protein:
(a) When the candidate compound is brought into contact with a cell, the amyloid β protein generation is decreased by 10% or more, preferably 25% or more, more preferably 50% or more, further preferably 75% or more, in comparison with the case where the candidate compound is not present;
(b) When the candidate compound is brought into contact with a cell, APP-CTF is decreased by 10% or more, preferably 25% or more, more preferably 50% or more, further preferably 75% or more, compared with the case where the candidate compound is not present;
(c) When the candidate compound is brought into contact with a cell, the Notch cleavage level is not decreased or is preferably decreased by less than 10%, compared with the case where the candidate compound is not present;

The method for detecting amyloid β protein and APP-CTF is not particularly limited insofar as it is capable of quantitative determination of amyloid β protein and APP-CTF; examples of the methods include analysis methods using ELISA, protein chip, western blotting, and the like.

The Notch cleavage level may be detected, for example, by a method of detecting NICD (Notch intracellular domain) that is released by the cleavage by γ-secretase. The method for detecting NICD is not particularly limited insofar as it is capable of quantitative determination of NICD. Examples of the methods include analysis methods using ELISA, protein chip, western blotting, and the like.

The "APP-CTF" above means membrane-spanning C-terminal fragment (CTF) of APP. Among APP-CTF, APP-C99 is particularly preferable as it is directly involved in Aβ generation.

The compound selected through the above method having activity similar to that of ILEI may be effective for the treatment and prevention of a disease involving abnormal accumulation of amyloid β protein (in particular, Alzheimer's disease).

EXAMPLES

Hereinbelow, Test Examples with regard to the present invention are described below. The present invention is, however, not limited to these examples.

Method

Plasmids

A cDNA encoding ILEI/FAM3C with or without the stop codon was amplified from a human brain cDNA library (Clontech) using PCR, and was then inserted into pcDNA6/V5-His (Invitrogen). To construct the ILEI knockdown vector, the oligonucleotide 5'-GGAGAAGUAUUAGA-CACU-3' (SEQ ID NO: 3) was inserted into pSUP (Oligoengine). To prepare an expression plasmid for siRNA-resistant ILEI, five neutral mutations were introduced into ILEI cDNA using PCR-based site-directed mutagenesis. The sequences of all constructs were confirmed by sequencing.

Antibody

Anti-human ILEI polyclonal antibody (ILEI-C) was raised in rabbits against a thyroglobulin-conjugated synthetic polypeptide corresponding to amino acid residues 126 to 143 with an added N-terminal Cys residue (C+GGDVAP-FIEFLKAIQDGT; SEQ ID NO: 4). This antibody was purified using immunoaffinity chromatography with immobilized antigen. The following antibodies were also used in this study: rabbit polyclonal anti-APP-CTF antibody and mouse monoclonal anti-β-actin antibodies (Sigma); mouse monoclonal anti-Notch-1 antibody (AbD Serotec); and mouse monoclonal anti-human Aβ antibody (4G8, Covance).

RNA Interference

The following siRNA duplexes were purchased from Dharmacon: siGENOME SMART pool M-020514 for ILEI knockdown and D001210 for a non-targeting control. The M-020514 pool consisted of the four duplexes targeting the following sequences: F1: 5'-GAACAGCA-CAUAAAGAACA-3'(SEQ ID NO: 5); F2: 5'-GGA-GAAGUAUUAGACACUA-3'(SEQ ID NO: 6); F3: 5'-GGAGCACAUCUAUUACUAA-3'(SEQ ID NO: 7); and F4: 5'-GAACAAUAAGGAUACAAAC-3' (SEQ ID NO: 8). Cultured cells were transfected with siRNA duplexes using Lipofectamine RNAi MAX (Invitrogen).

Immunoblotting

Brain homogenates were lysed in a buffer (25 mM HEPES, pH 7.5, 150 mM NaCl, 2 mM EDTA, protease inhibitor cocktail and 10% glycerol) containing 1% Nonidet P40. Immunoblotting was performed as previously described (Nishimura, M., et al. Nat Med 5, 164-169 (1999)).

Immunohistochemistry

The left halves of mouse brains were fixed in 4% paraformaldehyde in phosphate buffer for 24 hours at 4° C., and were then cut into 20-μm-thick floating sections in a Cryostat. The sections were incubated in 0.3% $H_2O_2$ in PBS for 30 min, then with each of the primary antibodies for 24 hours at 4° C., followed by incubation with a biotinylated secondary antibody and subsequently an avidin/biotinylated horseradish peroxidase complex (Vector Laboratories). Immunoreactivity was detected using 0.03% 3,3'-diaminobenzidine tetrahydrochloride containing 0.003% $H_2O_2$ and 0.5 mg ml$^{-1}$ ammonium nickel sulfate hexahydrate.

ILEI-Tg Mice

The transgenic vector pMoPrP-ILEI was constructed by subcloning an XhoI-XhoI fragment of human ILEI cDNA into the XhoI site of the MoPrP vector that contains the mouse prion promoter to achieve neuron-specific expression. Transgenic mice were generated by injection of pMoPrP-ILEI DNA into fertilized C57BL/6 mouse oocytes using standard techniques. Transgenic founders were identified using PCR (see below). The genotypes of transgenic mice were determined by PCR using the following transgene-specific primer pair: mPrP-s5'-CTGCTCCATTTTGCGT-GACTC-3' (SEQ ID NO: 9) and hFAM3C-as 5'-CTTCCA-GGCAGATTTTGGGTC-3' (SEQ ID NO: 10).

Measurement of Aβ

Using this cell culture solution, the measurement of secretory Aβ from the cells was performed according to ELISAs specific for human Aβ40 and Aβ42 (Wako Pure Chemical Industries).

For the measurement of Aβ in the mouse brains, the right halves of mouse brains were homogenized using a motor-driven Teflon/glass homogenizer (10 strokes) in 4 volumes of Tris buffer (20 mM Tris, pH 7.5, 150 mM NaCl, 0.5 mM EDTA). The homogenates were centrifuged at 100,000×g for 20 min. The supernatant was used as the soluble fraction. The pellet was lysed by brief sonication in 1 volume of 6 M guanidine hydrochloride in 50 mM Tris, pH 7.5, then centrifuged at 100,000×g for 10 min. The supernatant was diluted at 1:12 and used as the insoluble fraction. The soluble and insoluble fractions were subjected to a DC protein assay (BioRad) and ELISAs specific for mouse/rat Aβ40 and Aβ42 (IBL). The Aβ concentration was found as molar concentration based on the total protein weight.

Statistical Analysis

Statistical evaluation was performed using Student's unpaired t-test. Data are presented as means±s.d. (standard deviation). Statistical significance was defined as *$p<0.05$ or **$p<0.01$.

Test Example 1

Figure 1:
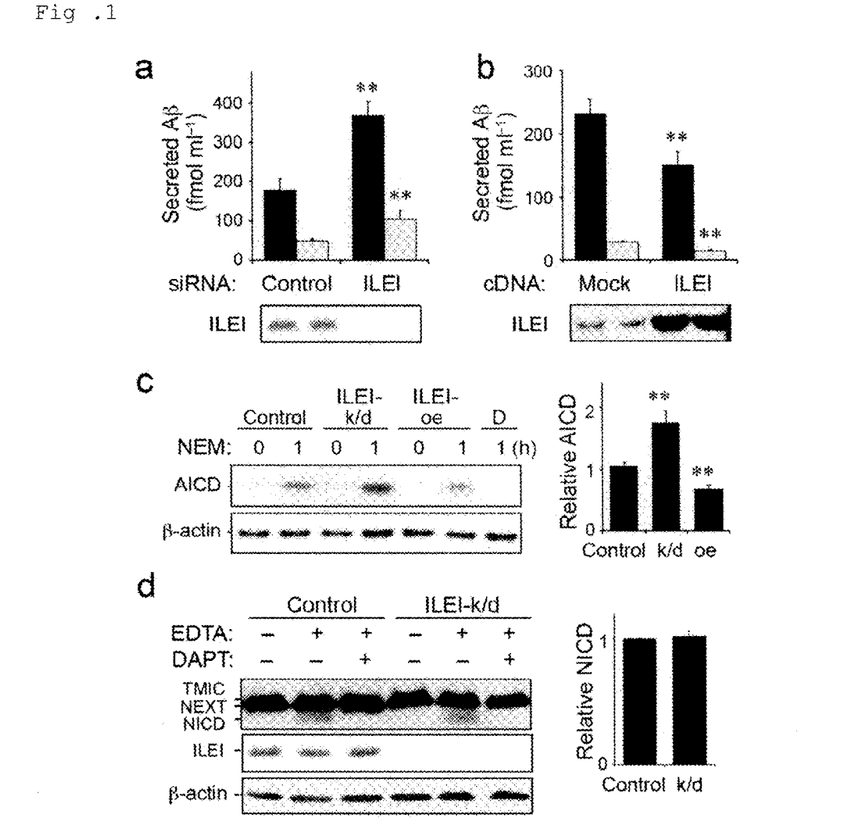
FIG. 1 shows graphs presenting the results of Test Example 1. (a) and (b) black bar: Aβ40, gray bar: Aβ42, : p<0.01 versus Control or Mock. (c) The immunoblot shown is representative of three independent experiments. : p<0.01 versus Control

Control or ILEI-specific siRNA was transiently transfected into HEK293 cells. Aβ40 (black bars) and Aβ42 (gray bars) in the culture solution were measured using ELISAs (FIG. 1a). FIG. 1a shows that RNAi-mediated knockdown of endogenous ILEI in HEK293 cells resulted in an approximately 2-fold increase in Aβ40 and Aβ42 levels in the conditioned media.

Mock or ILEI cDNA was transiently transfected into HEK293 cells. Aβ40 (black bars) and Aβ42 (gray bars) in the culture solution were measured using ELISAs (FIG. 1b). FIG. 1b shows that overexpression of ILEI decreased Aβ secretion by HEK293 cells.

HEK293 cells transfected with control, ILEI siRNA, or ILEI cDNA (respectively denoted by ILEI-k/d and ILEI-oe in the figure) were treated with N-ethyl maleimide (NEM) for 60 minutes to block degradation of AICD. The AICD production was inhibited by a treatment with DAPT, which is a γ-secretase inhibitor (D in the figure). β-Actin was used as a loading control. The graphs show quantified AICD signal intensities (n=3). FIG. 1c shows that ILEI knockdown increased AICD production, and ILEI overexpression decreased AICD production.

Next, γ-secretase cleavage of endogenous Notch-1 in mouse embryonic fibroblasts (MEFs) was examined (FIG. 1d). Treatment of MEF with EDTA (1.5 mM) induces cleavage of TMIC (transmembrane/intracellular Notch) and generates NEXT (Notch extracellular truncation). NEXT is further cleaved by γ-secretase to release NICD (Notch intracellular domain). The NICD production was inhibited by DAPT (1 μM). β-Actin was used as a loading control. The graphs show quantified NICD signal intensities (n=3). FIG. 1d shows that ILEI knockdown did not alter the generation of NICD in the presence of EDTA. These findings suggested that ILEI does not perturb Notch cleavage by γ-secretase.

Test Example 2

Figure 2:
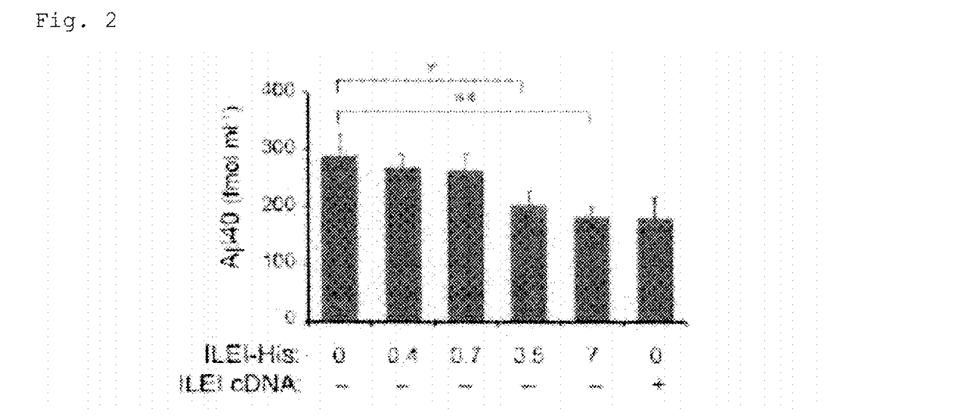
FIG. 2 shows a graph presenting the results of Test Example 2. *: p<0.05, **: p<0.01

Purified ILEI-His was added into the culture solution of stable ILEI-knockdown HEK293 cells at the indicated concentration (μg ml$^{-1}$). FIG. 2 shows the results. Administration of purified ILEI-His diminished Aβ secretion in a dose-dependent manner. At a concentration of 7 μg ml$^{-1}$, Aβ secretion was decreased to almost the same extent as in the case of introducing siRNA-resistant ILEI cDNA.

Test Example 3

To analyze the consequences of ILEI overexpression in mammalian brains, transgenic (Tg) mice were developed by using mouse prion (PrP) promoter to drive expression of a human ILEI cDNA transgene predominantly in brains. The heterozygous Tg mice exhibited normal development and fertility without any gross morphological defect.

Figure 3:
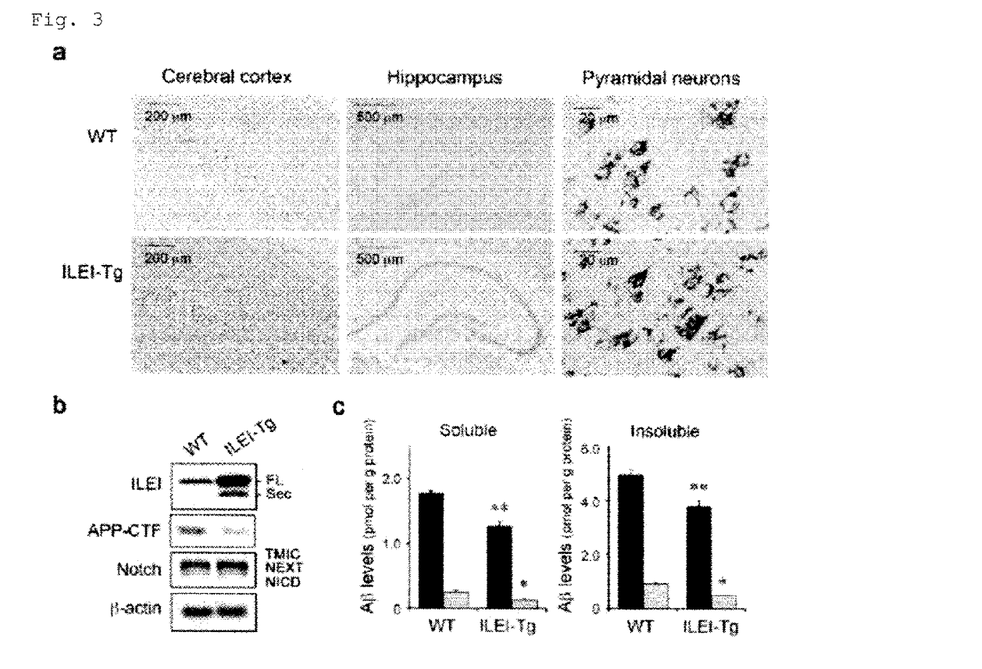
FIG. 3 consists of pictures showing the results of Test Example 3. (b) FL: full-length, Sec: secreted form. (c) black bar: Aβ40, gray bar: Aβ42, *: p<0.05 versus WT, **: p<0.01 versus WT

FIG. 3a indicated by immunohistochemistry that ILEI is expressed in neuron cells in the cerebral cortex and hippocampus of wild-type (WT) and ILEI-Tg mouse brains. Similar to wild-type mice, ILEI expression was restricted to neuron cells in Tg mouse brains.

Brain homogenates of 6-week-old ILEI-Tg mice and their wild-type littermates were subjected to immunoblotting. β-Actin was assayed as a loading control. Immunoblotting of brain homogenates indicated a 3-fold increase in ILEI protein levels in the Tg mice compared with wild-type littermates (FIG. 3b). It also revealed a 30% decease in APP-CTF levels in the brains of the Tg mice, and no alteration of NICD levels in the brains of the Tg mice.

Aβ40 (black bars) and Aβ42 (gray bars) in Tris-buffered saline-soluble and insoluble fractions of brain homogenates were measured using ELISAs (8 months old, n=5). Aβ40 and Aβ42 levels of both fractions were significantly reduced in ILEI-Tg mice comparing with their wild-type littermates (FIG. 3c). These results suggested that overexpressed ILEI suppresses APP-CTF accumulation and Aβ generation in the brains of individual mice, while sparing Notch cleavage.

The invention claimed is:

1. A method of treating a disease involving abnormal accumulation of amyloid β protein in a subject in need thereof, comprising administering to the subject interleukin-like epithelial-mesenchymal transition inducer (ILEI).

2. The method according to claim 1, wherein the disease involving abnormal accumulation of amyloid β protein is Alzheimer's disease.

3. The method according to claim 1, wherein the ILEI is a protein comprising the amino acid sequence of SEQ ID NO: 1, in which from 0 to 5 amino acids are substituted, deleted or added.

4. The method according to claim 1, wherein the ILEI is a protein comprising the amino acid sequence of SEQ ID NO: 2, in which from 0 to 5 amino acids are substituted, deleted or added.

5. The method according to claim 1, wherein the ILEI is a protein comprising the amino acid sequence of SEQ ID NO: 2.

6. The method according to claim 1, wherein the ILEI is a protein comprising the amino acid sequence of SEQ ID NO: 1.

* * * * *

SEQUENCE LISTING

```
<160> NUMBER OF SEQ ID NOS: 10

<210> SEQ ID NO 1
<211> LENGTH: 227
<212> TYPE: PRT
<213> ORGANISM: Homo sapiens

<400> SEQUENCE: 1

Met Arg Val Ala Gly Ala Ala Lys Leu Val Val Ala Val Ala Val Phe
1               5                   10                  15

Leu Leu Thr Phe Tyr Val Ile Ser Gln Val Phe Glu Ile Lys Met Asp
            20                  25                  30

Ala Ser Leu Gly Asn Leu Phe Ala Arg Ser Ala Leu Asp Thr Ala Ala
        35                  40                  45

Arg Ser Thr Lys Pro Pro Arg Tyr Lys Cys Gly Ile Ser Lys Ala Cys
    50                  55                  60

Pro Glu Lys His Phe Ala Phe Lys Met Ala Ser Gly Ala Ala Asn Val
65                  70                  75                  80

Val Gly Pro Lys Ile Cys Leu Glu Asp Asn Val Leu Met Ser Gly Val
                85                  90                  95

Lys Asn Asn Val Gly Arg Gly Ile Asn Val Ala Leu Ala Asn Gly Lys
            100                 105                 110

Thr Gly Glu Val Leu Asp Thr Lys Tyr Phe Asp Met Trp Gly Gly Asp
        115                 120                 125

Val Ala Pro Phe Ile Glu Phe Leu Lys Ala Ile Gln Asp Gly Thr Ile
    130                 135                 140

Val Leu Met Gly Thr Tyr Asp Asp Gly Ala Thr Lys Leu Asn Asp Glu
145                 150                 155                 160

Ala Arg Arg Leu Ile Ala Asp Leu Gly Ser Thr Ser Ile Thr Asn Leu
                165                 170                 175

Gly Phe Arg Asp Asn Trp Val Phe Cys Gly Gly Lys Gly Ile Lys Thr
            180                 185                 190
```

```
Lys Ser Pro Phe Glu Gln His Ile Lys Asn Asn Lys Asp Thr Asn Lys
        195                 200                 205

Tyr Glu Gly Trp Pro Glu Val Val Glu Met Glu Gly Cys Ile Pro Gln
210                 215                 220

Lys Gln Asp
225

<210> SEQ ID NO 2
<211> LENGTH: 203
<212> TYPE: PRT
<213> ORGANISM: Homo sapiens

<400> SEQUENCE: 2

Gln Val Phe Glu Ile Lys Met Asp Ala Ser Leu Gly Asn Leu Phe Ala
1               5                   10                  15

Arg Ser Ala Leu Asp Thr Ala Ala Arg Ser Thr Lys Pro Pro Arg Tyr
            20                  25                  30

Lys Cys Gly Ile Ser Lys Ala Cys Pro Glu Lys His Phe Ala Phe Lys
        35                  40                  45

Met Ala Ser Gly Ala Ala Asn Val Val Gly Pro Lys Ile Cys Leu Glu
50                  55                  60

Asp Asn Val Leu Met Ser Gly Val Lys Asn Asn Val Gly Arg Gly Ile
65                  70                  75                  80

Asn Val Ala Leu Ala Asn Gly Lys Thr Gly Glu Val Leu Asp Thr Lys
                85                  90                  95

Tyr Phe Asp Met Trp Gly Gly Asp Val Ala Pro Phe Ile Glu Phe Leu
            100                 105                 110

Lys Ala Ile Gln Asp Gly Thr Ile Val Leu Met Gly Thr Tyr Asp Asp
        115                 120                 125

Gly Ala Thr Lys Leu Asn Asp Glu Ala Arg Arg Leu Ile Ala Asp Leu
130                 135                 140

Gly Ser Thr Ser Ile Thr Asn Leu Gly Phe Arg Asp Asn Trp Val Phe
145                 150                 155                 160

Cys Gly Gly Lys Gly Ile Lys Thr Lys Ser Pro Phe Glu Gln His Ile
                165                 170                 175

Lys Asn Asn Lys Asp Thr Asn Lys Tyr Glu Gly Trp Pro Glu Val Val
            180                 185                 190

Glu Met Glu Gly Cys Ile Pro Gln Lys Gln Asp
        195                 200

<210> SEQ ID NO 3
<211> LENGTH: 18
<212> TYPE: RNA
<213> ORGANISM: Artificial Sequence
<220> FEATURE:
<223> OTHER INFORMATION: To construct the ILEI knockdown vector, the
      oligonucleotide was ligeted into pSUP.

<400> SEQUENCE: 3
ggagaaguau uagacacu                                                18

<210> SEQ ID NO 4
<211> LENGTH: 19
<212> TYPE: PRT
<213> ORGANISM: Artificial Sequence
<220> FEATURE:
<223> OTHER INFORMATION: ILEI 126-143

<400> SEQUENCE: 4
```

```
Cys Gly Gly Asp Val Ala Pro Phe Ile Glu Phe Leu Lys Ala Ile Gln
1               5                   10                  15

Asp Gly Thr

<210> SEQ ID NO 5
<211> LENGTH: 19
<212> TYPE: RNA
<213> ORGANISM: Artificial Sequence
<220> FEATURE:
<223> OTHER INFORMATION: siRNA

<400> SEQUENCE: 5
gaacagcaca uaaagaaca                                            19

<210> SEQ ID NO 6
<211> LENGTH: 19
<212> TYPE: RNA
<213> ORGANISM: Artificial Sequence
<220> FEATURE:
<223> OTHER INFORMATION: siRNA

<400> SEQUENCE: 6
ggagaaguau uagacacua                                            19

<210> SEQ ID NO 7
<211> LENGTH: 19
<212> TYPE: RNA
<213> ORGANISM: Artificial Sequence
<220> FEATURE:
<223> OTHER INFORMATION: siRNA

<400> SEQUENCE: 7
ggagcacauc uauuacuaa                                            19

<210> SEQ ID NO 8
<211> LENGTH: 19
<212> TYPE: RNA
<213> ORGANISM: Artificial Sequence
<220> FEATURE:
<223> OTHER INFORMATION: siRNA

<400> SEQUENCE: 8
gaacaauaag gauacaaac                                            19

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
ctgctccatt ttgcgtgact c                                         21

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
cttccaggca gattttgggt c                                         21
```